(12) United States Patent  
Haines

(10) Patent No.: US 7,914,586 B2
(45) Date of Patent: Mar. 29, 2011

(54) PROSTHETIC DEVICE UTILIZING ELECTRIC VACUUM PUMP

(75) Inventor: Wilbur A. Haines, Indianapolis, IN (US)

(73) Assignee: The Ohio Willow Wood Company, Mount Sterling, OH (US)

( * ) Notice: Subject to any disclaimer, the term of this patent is extended or adjusted under 35 U.S.C. 154(b) by 1372 days.

(21) Appl. No.: 11/149,858

(22) Filed: Jun. 10, 2005

(65) Prior Publication Data

US 2006/0282174 A1    Dec. 14, 2006

(51) Int. Cl.
*A61F 2/48* (2006.01)
*A61F 2/60* (2006.01)
*A61F 2/78* (2006.01)

(52) U.S. Cl. .......................................... 623/24; 623/33
(58) Field of Classification Search .................. 623/24
See application file for complete search history.

(56) References Cited

U.S. PATENT DOCUMENTS

| | | | | |
|---|---|---|---|---|
| 5,112,296 A * | 5/1992 | Beard et al. | ...................... | 602/28 |
| 5,336,270 A * | 8/1994 | Lloyd | .............................. | 623/33 |
| 5,549,709 A * | 8/1996 | Caspers | .......................... | 623/24 |
| 5,658,353 A | 8/1997 | Layton | | |
| 5,735,906 A * | 4/1998 | Caspers | .......................... | 623/34 |
| 5,807,397 A | 9/1998 | Barreras | | |
| 5,840,047 A | 11/1998 | Stedham | | |
| 5,888,212 A * | 3/1999 | Petrofsky et al. | ................ | 623/24 |
| 5,904,722 A * | 5/1999 | Caspers | .......................... | 623/34 |
| 6,063,125 A | 5/2000 | Arbogast et al. | | |
| 6,137,889 A | 10/2000 | Shennib et al. | | |
| 6,508,842 B1 * | 1/2003 | Caspers | .......................... | 623/32 |
| 6,554,868 B1 * | 4/2003 | Caspers | .......................... | 623/34 |
| 6,585,774 B2 | 7/2003 | Dean | | |
| 6,610,096 B2 | 8/2003 | MacDonald | | |
| 6,645,253 B2 | 11/2003 | Caspers | .......................... | 623/26 |
| 6,726,726 B2 | 4/2004 | Caspers | .......................... | 623/34 |
| 6,761,742 B2 | 7/2004 | Caspers | .......................... | 623/34 |
| 6,905,519 B2 | 6/2005 | Swanson | | |
| 6,926,742 B2 | 8/2005 | Caspers et al. | | |
| 6,974,484 B2 | 12/2005 | Caspers | .......................... | 623/34 |
| 7,029,500 B2 | 4/2006 | Martin | | |
| 2001/0016781 A1 * | 8/2001 | Caspers | .......................... | 623/34 |
| 2002/0120349 A1 * | 8/2002 | Phillips | .......................... | 623/35 |
| 2004/0019382 A1 | 1/2004 | Amirouche et al. | | |
| 2004/0030411 A1 | 2/2004 | Caspers | .......................... | 623/37 |
| 2004/0143345 A1 | 7/2004 | Caspers | .......................... | 623/36 |
| 2004/0181290 A1 | 9/2004 | Caspers | .......................... | 623/34 |
| 2006/0085082 A1 * | 4/2006 | Asgeirsson et al. | ............ | 623/26 |
| 2006/0136072 A1 * | 6/2006 | Bisbee et al. | .................... | 623/24 |
| 2006/0212128 A1 * | 9/2006 | Nachbar | .......................... | 623/24 |
| 2007/0112439 A1 | 5/2007 | Panucialman | | |

* cited by examiner

*Primary Examiner* — David Isabella
*Assistant Examiner* — Jacqueline Woznicki
(74) *Attorney, Agent, or Firm* — Standley Law Group LLP

(57) ABSTRACT

An artificial limb using a vacuum attachment principle is provided with an electrically activated pump that may be readily incorporated into the artificial limb or into a separate portable device. Because the electrically activated pump does not require manual manipulation to create vacuum, it is substantially easier to use than a manual pump. Due to the small size and small battery required by the electrically activated pump disclosed here, it may be readily incorporated into a prosthesis.

17 Claims, 6 Drawing Sheets

PROSTHETIC DEVICE UTILIZING ELECTRIC VACUUM PUMP

FIELD OF THE INVENTION

The present invention relates to prosthetic limbs.

BACKGROUND OF THE INVENTION

Artificial limbs have been in use throughout history, having been first recorded circa 2750 B.C. During that period of time, interfacing and suspending an artificial limb has been a continuing challenge. Various and numerous theories and anatomical constructs have been used over time in an evolving manner, and these have revealed a number of key factors in maximizing comfort and functional potential for persons who wear artificial limbs.

Firstly, the surgical procedure used to perform limb amputation is an important factor. The size and shaping of the patient's residual limb is often important to the comfort the patient will later have with a prosthesis. Stated simply, it is critical that the residual limb and prosthesis interface tightly and couple and distribute pressure evenly across the surface of the residual limb.

Early versions of artificial limbs required the use of leather or equivalent straps or belts to suspend the artificial limb upon the person. Later systems employed linkage techniques such as condylar wedges, rubber or synthetic elastic tubing, thermoplastic roll-on sleeves with pin locking systems, and sub atmospheric pressure. Of these, sub atmospheric pressure is typically preferred, because it creates a linkage that provides maximum proprioceptive feedback and control for the artificial limb user. It also provides the best linkage between the user's limb and the prosthetic device.

Creating a reliable sub atmospheric pressure chamber between the residual limb and prosthetic device has, however, proved to be a challenge. As new airtight thermoplastic and thermo set materials have evolved, along with airtight thermoplastic roll-on liners, the potential for creating a sub atmospheric pressure within the prosthetic chamber has improved. Specifically, the patient's residual limb is covered with a roll-on urethane or other thermoplastic liner, which helps to protect the user's tissue from unwanted isolated high negative pressure values, and provides cushioning for the tissue at the same time. The liner also helps to distribute the sub atmospheric pressure applied to the user's limb in a more uniform manner.

Several means for creating an elevated negative pressure chamber within the artificial limb interface have emerged. One method disclosed in U.S. Pat. No. 6,554,868, utilizes a weight activated pump, in which sub atmospheric pressure is maintained strategically within the artificial limb interface cavity as the user walks. This approach has the advantage of continuing maintenance of vacuum as the patient ambulated with the artificial limb. However, the problem with this method is that the pump is heavy, and cannot be removed even in the case of a pump failure. Furthermore, the pump requires a certain minimum space between the user's limb and prosthetic foot, which may be more than is available if the patient has a relatively long residual limb. This prohibits the use of this technology for many artificial limb users. Another disadvantage of this system is that it requires a number of weight activated strokes before the sub atmospheric pressure pump linkage system becomes effective.

Another method disclosed in the above-referenced patent uses a hand-held sub atmospheric pressure pump, much like that used to bleed brake systems on an automobile. This method works well, but requires the individual to carry the hand-held pump upon their person to use in case of vacuum failure. It is also awkward to use for many individuals and requires a certain amount of dexterity and strength to operate. This is a common problem for elderly individuals.

Thus, there is a need for improved technology for achieving sub atmospheric pressure within an artificial limb chamber.

SUMMARY OF THE INVENTION

The present invention improves upon the available known prosthetic technology by providing an artificial limb with an electrically activated pump that may be readily incorporated into the artificial limb. Because the electrically activated pump does not require manual manipulation to create vacuum, it is substantially easier to use than a manual pump. Due to the small size and small battery required by the electrically activated pump disclosed here, it may be readily incorporated into a prosthesis.

This arrangement thus affords substantial advantages over the manual pumps and gait-driven pumps of the prior art, and the inventors are believed to be the first to present a practical approach to providing an electrically evacuated prosthetic device. The '868 patent referenced above suggests the inclusion of a generically drawn "vacuum source" and "power source", and a regulator for automatic vacuum maintenance, into an outer socket of a prosthesis (see, e.g., FIGS. 7 and 9 and discuss thereof); however, there is no specific reference therein to a vacuum source or power source that is of suitable size and weight for such an application, as is provided by the inventors hereof. The present invention thus represents an advance and an enabled approach to providing electrically actuated, portable vacuum pump in a prosthesis.

The above and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION OF SPECIFIC EMBODIMENTS

Figure 1:
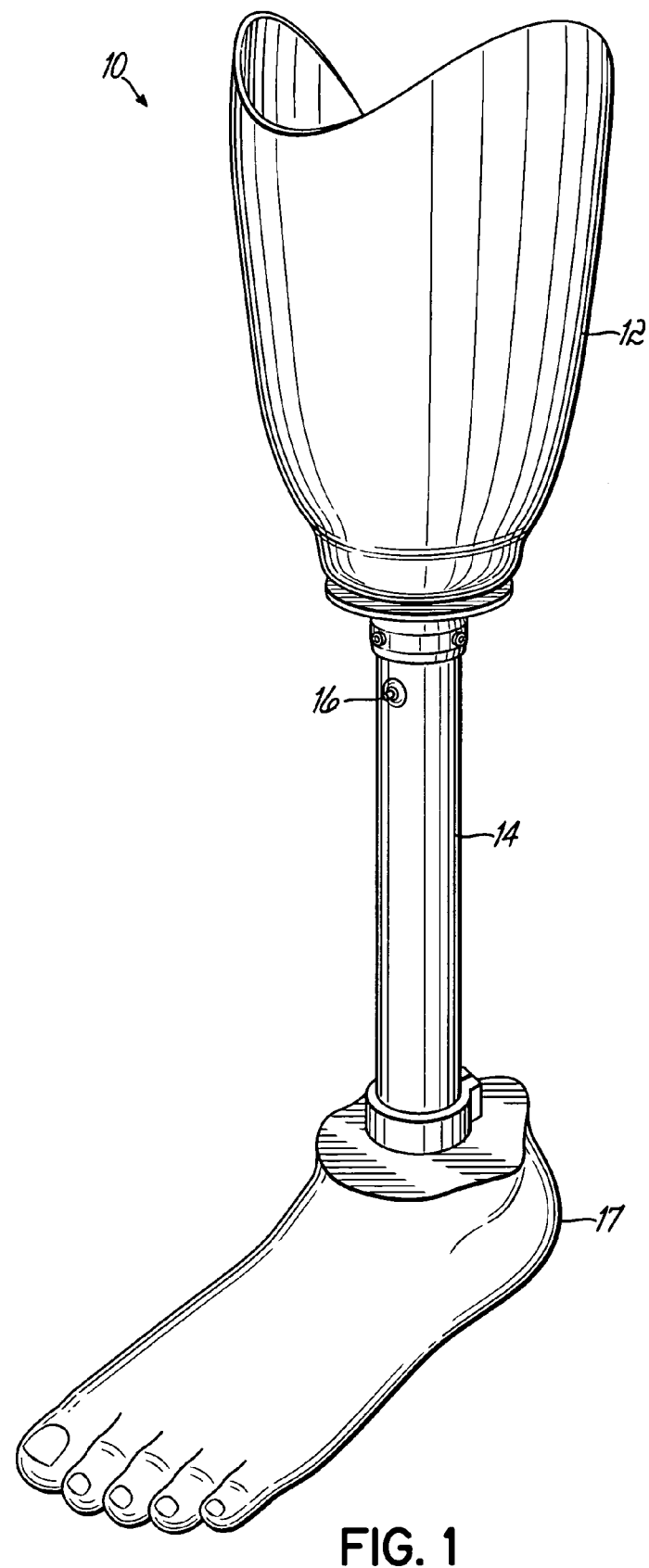
FIG. 1 illustrates a prosthetic limb incorporating an electric vacuum pump in accordance with principles of the present invention.

FIG. 1 illustrates a prosthesis 10 in accordance with principles of the present invention. The prosthesis includes a socket 12 for receiving the patient's residual limb, a column 14, typically a cylindrical section of lightweight metal such as aluminum, and an artificial foot 17. As can be seen on FIG. 1, column 14 includes a vacuum actuator button 16 used to actuate an electric vacuum pump within the column, to draw air from the socket 12 to draw the residual limb into intimate contact with socket 12.

Figure 2:
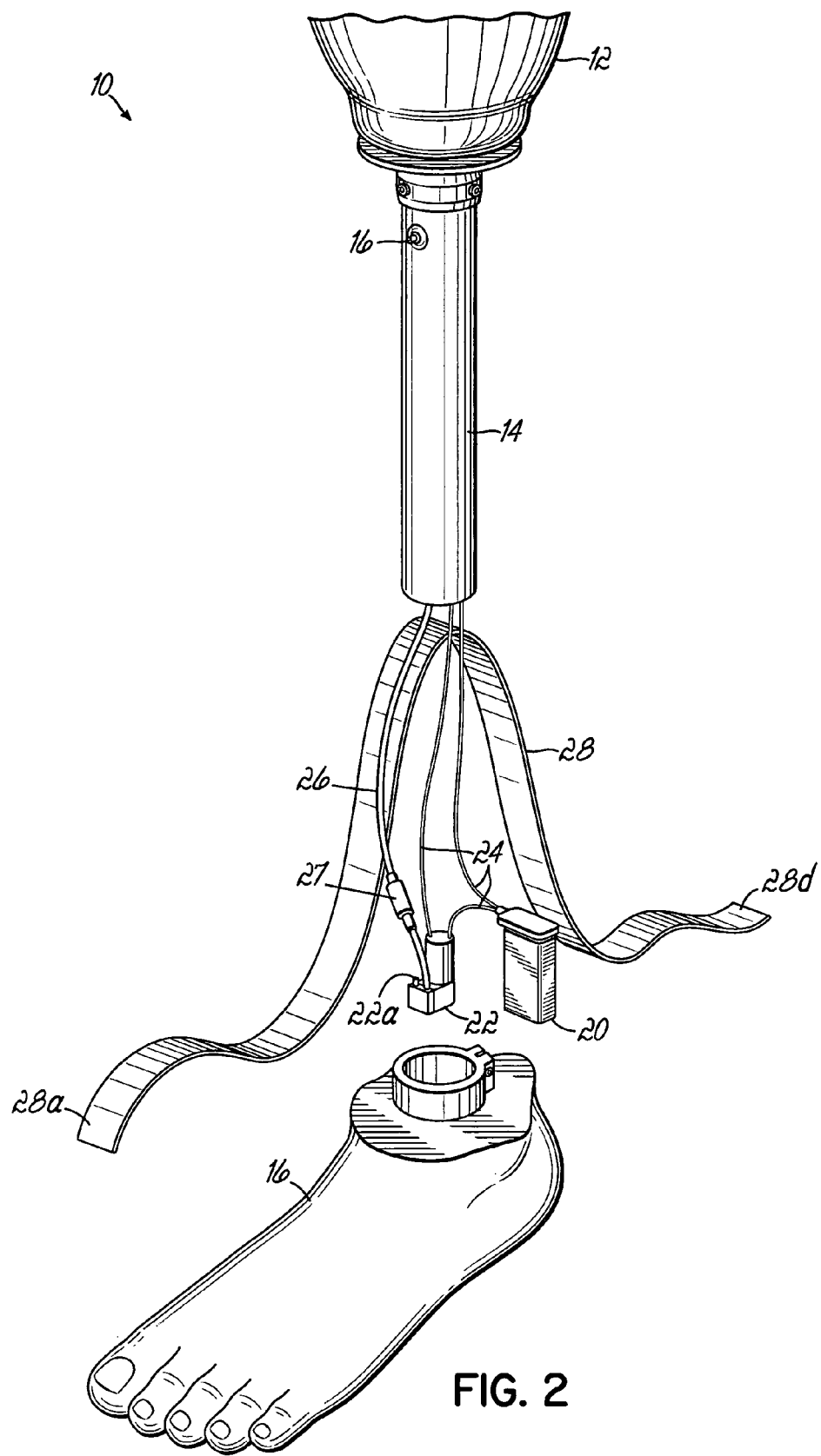
FIG. 2 is a disassembled view of the limb of FIG. 1, illustrating internal components thereof.

FIG. 2 illustrates the prosthesis of FIG. 1 disassembled to show the component parts within post 14. Internal to post 14 is a battery 20, such as a conventional 9-volt battery, a vacuum pump 22, and electrical lines 24 for delivering electrical power from battery 20 to vacuum pump 22, and vacuum line 26 for drawing vacuum from socket 12 through a check valve 27. Components 20, 22, 24, 26 and 27 are inserted into post 14 after insertion of a ribbon 28, so that ribbon 28 may be used to remove those components, e.g. for changing battery 20.

A suitable vacuum pump for use as vacuum pump 22 (or for vacuum pump 62 in the alternative embodiment of FIG. 5) is the model VMP 1624 Series vacuum pump, available from Virtual Industries, Inc., 2130 Vector Place, Colorado Springs Colo. The specific model suitable for application as shown herein is model 1624-009-S. This family of pumps is capable of drawing vacuum up to 18 inches of mercury (−594 millibar), which is sufficient for use in a prosthesis. The pump flow rate is as large as 1300 mm per minute. The motor of this pump is manufactured by Faulhaber GmbH & Co. KG, at Postfach 1146, D-71094 Schönaich, Germany. An alternative motor is made by Canon. Maxon in Switzerland is another vendor of small motors. The diaphragm included in the vacuum pump is made by Vinton. The voltage for the identified specific model is 9 volts, permitting use of the pump with a conventional 9-volt battery, such as the L-522 battery available from Eveready Battery Co. Inc. under the trademark "Energizer". Compatible 9 volt batteries are sold by other vendors such as by Mallory/Duracell as EN22/E22, by Rayovac as A1604/AL-9V, and by Panasonic as 6AM6. A rechargeable battery may also be used, such as a model LIPBA-300-8, an 8 volt lithium ion polymer battery rated at 300 mAh/8v, available from OPRA-TECH Engineering, Warren, Ohio.

Figure 5:
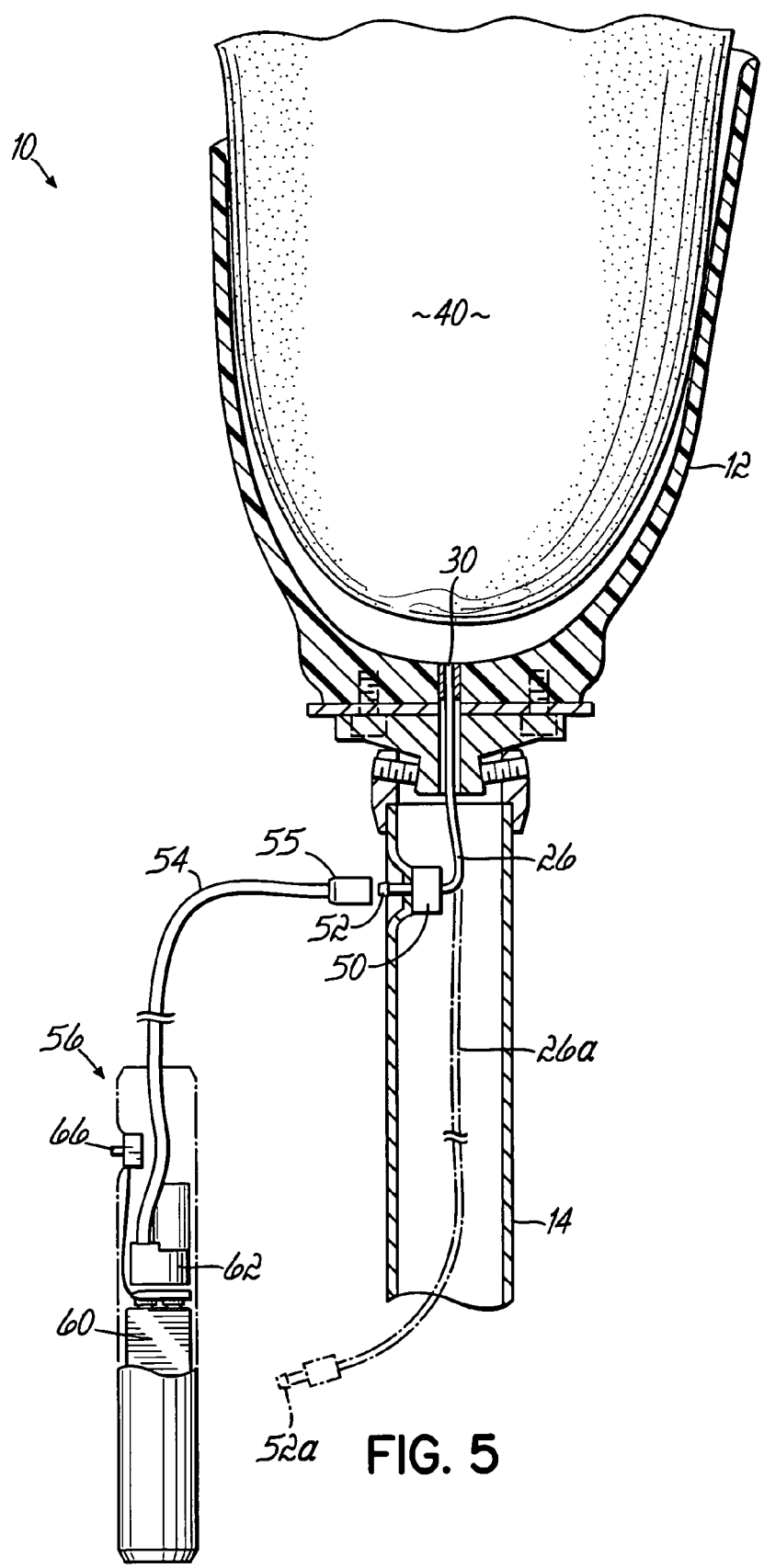
FIG. 5 illustrates an alternative embodiment in accordance with principles of the present invention, in which the electric pump and battery are housed in a separate portable vacuum pump.

The body of the identified pump is made of polyphenylene sulfide (PPS) glass fiber. The weight of the pump is approximately 1.1 oz. and it measures approximately 1.625 inches high by 0.625 inches wide by 1.0 inches depth. The weight of battery 20 is typically 1.3 oz. and it measures approximately 1.875 inches high by 1.0 inches wide by 0.625 inches deep. With these sizes and weights, the pump and battery may be easily fitted within the column 14 of the prosthetic limb without substantially increasing the effort and drain on the patient using the limb, or may be easily fitted within a portable inflation pump such as illustrated in FIG. 5 below.

Figure 3:
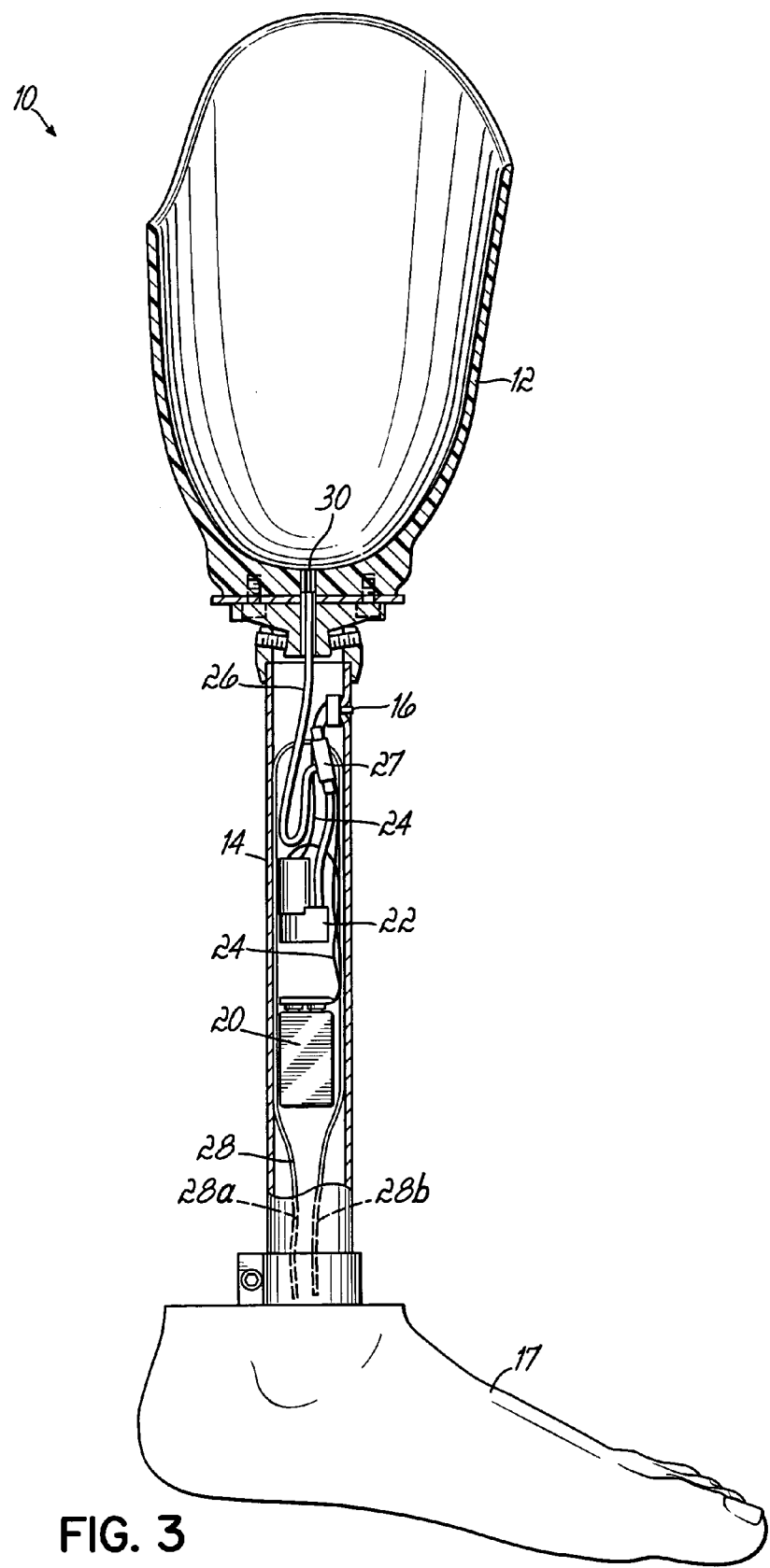
FIG. 3 is a cutaway view of the limb of FIG. 1 showing the internal components as positioned when the limb is in use.

FIG. 3 is a cross-sectional view of the prosthetic device 10 illustrating the components of FIG. 2 when inserted into post 14. As can be seen in FIG. 3, ribbon 28 forms a loop surrounding battery 20 and vacuum pump 22 so that those components may be removed by pulling at the ends 28A and 28B of ribbon which extends to the bottom end of post 14. FIG. 3 further illustrates the vacuum and electrical circuits formed by the various components of the prosthetic device 10. Specifically, an electrical circuit is formed by electrical connections. 24, the positive and negative contacts of battery 20 and the positive and negative terminals of vacuum pump 22. As can be seen, one electrical connection directly connects one terminal of battery 20 to one terminal of vacuum pump 22, and further electrical connections connect the other terminal of battery 20 to the other terminal of vacuum pump 22 via electrical switch 16. Thus, by closing electrical switch 16, battery voltage is applied to vacuum pump 22, causing vacuum pump 22 to operate and draw vacuum from socket 12.

A user of a prosthetic device as thus described can readily create elevated vacuum to any level desired, to the limits of vacuum that can be drawn by the pump 22. No particular vacuum level is required or contemplated by the present invention, as individual patients will have individual preferences and physical and/or physiological needs as to the amount of vacuum drawn. The described vacuum pump has a sufficient flow rate that a user will typically activate the vacuum pump for less than 30 seconds to draw the desired amount of vacuum from socket 12. Some users will require very little vacuum within the socket 12, whereas others will desire a higher level of vacuum and will draw vacuum for a longer period of time. Higher levels of vacuum can reduce the risk of ulceration and improve vascular flow. Furthermore, the patient may readily re-apply vacuum using the pump as described above even when remote from a power source.

As can be further seen in FIG. 3, vacuum line 26 connects vacuum pump 22 to a vacuum orifice 30 in socket 12 so that vacuum may be drawn from socket 12 during operation of vacuum pump 22. As seen in FIG. 2, air drawn from vacuum line 26 by vacuum pump 22 is expelled via a outlet port 22A on vacuum pump 22 into the interior of post 14. Air expelled into post 14 is vented to the atmosphere, as the interior of post 14 is not sealed from atmospheric pressure.

As can be seen in FIG. 2 and in FIG. 3, vacuum line 26 includes a check valve 27, such as duckbill-style valve, for permitting airflow through vacuum tube 26 to vacuum pump 22 but preventing reverse airflow from vacuum pump 22 through vacuum tube 26 and into socket 12.

Figure 4A:
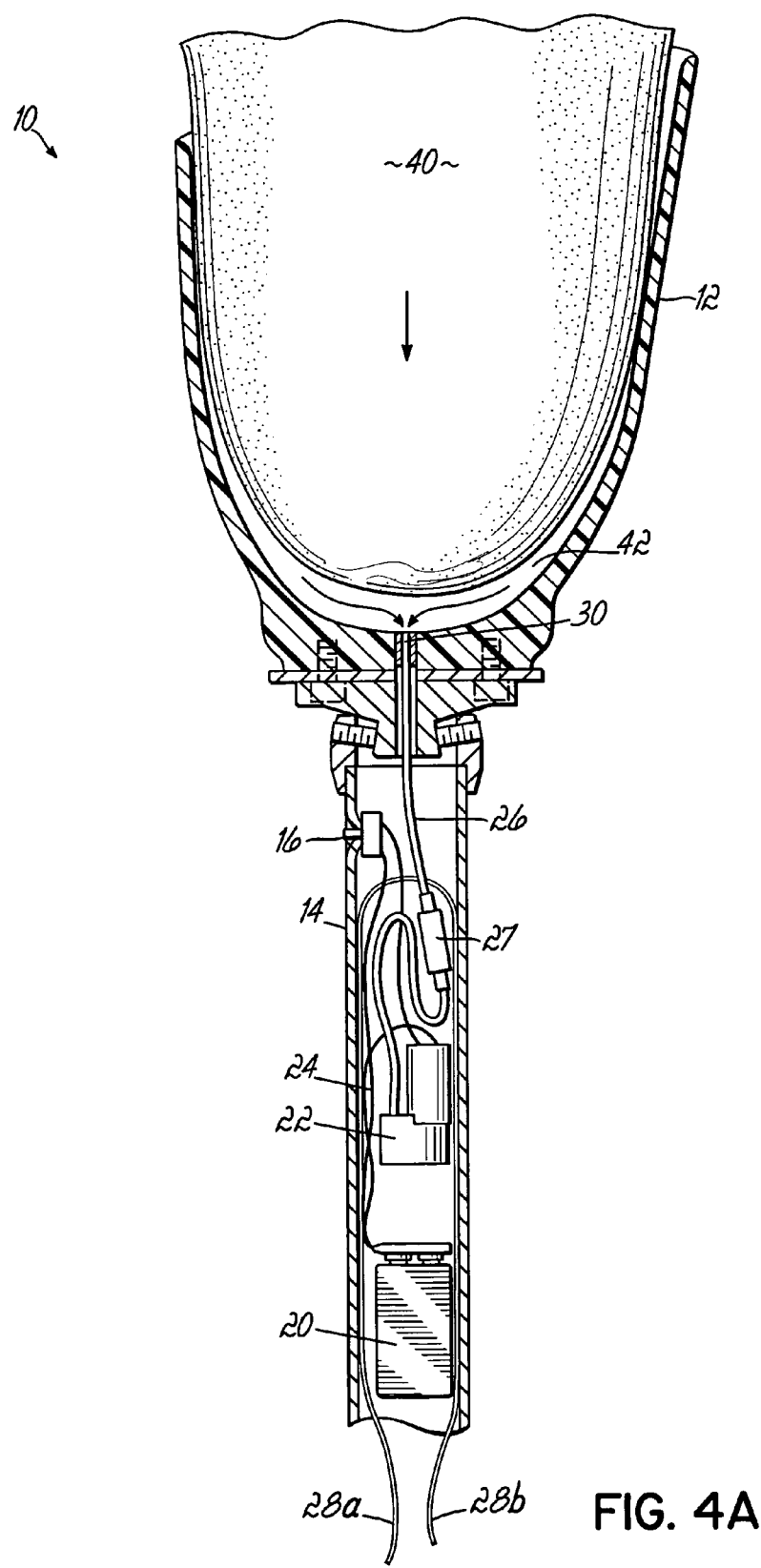
FIGS. 4A and 4B are cutaway views of the limb of FIG. 1 showing its use in creating vacuum engagement of a limb with a socket.
Figure 4B:
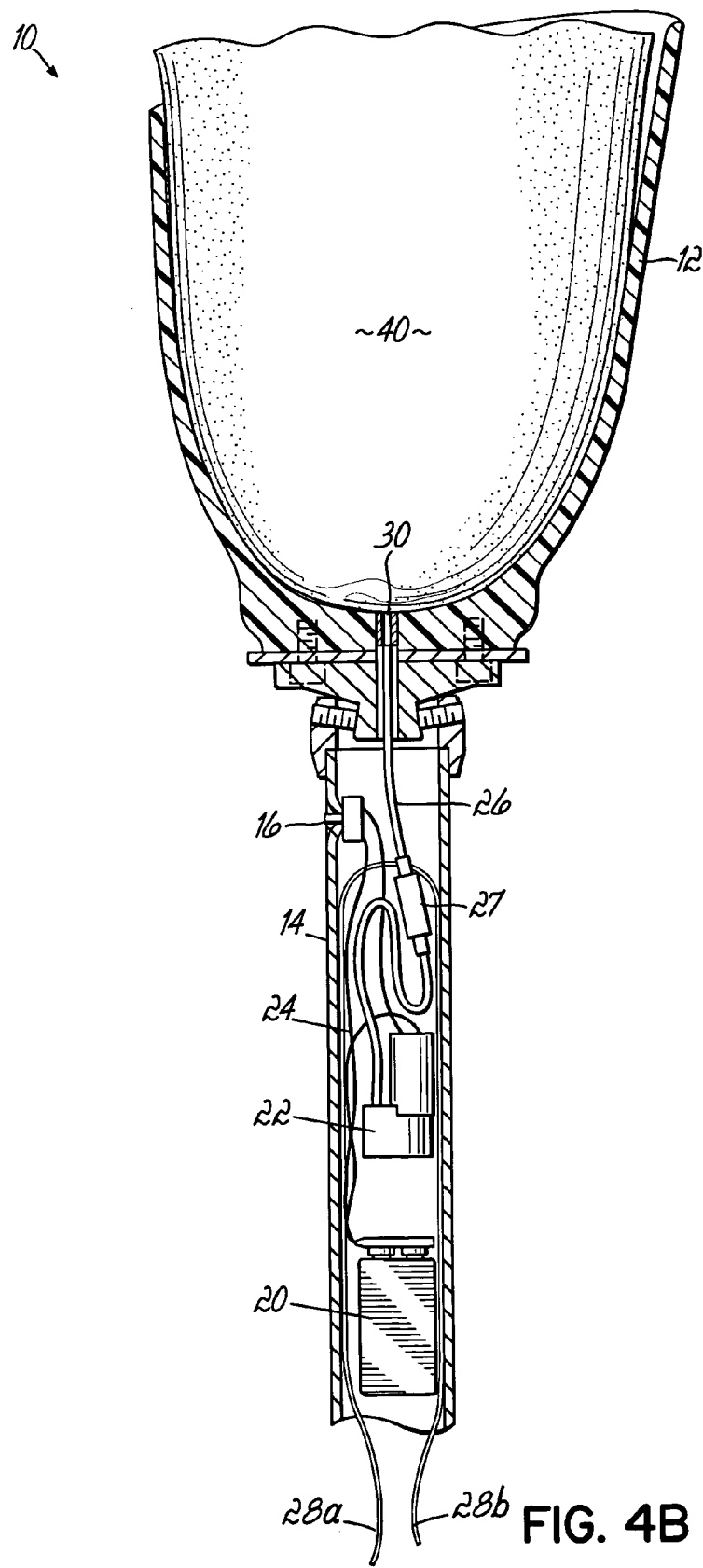

Referring now to FIG. 4A, use of the inventive prosthetic device 10 in connection with a patient's residual limb can be illustrated in further detail. As seen in FIG. 4A, patient's residual limb 40, typically having a liner and air wick sheath thereon, is inserted into socket 12, typically leaving a cavity 42 filled with air. (As is known to those skilled in the art, an air wick sheath such as fabric is used because the urethane or thermoplastic liner, by itself, would seal the vacuum orifice and thus limit the vacuum to the opening of the orifice only— the prosthetic sheath over the urethane liner allows air to be evacuated everywhere the sheath is upon the patient's limb.) Next, the patient actuates button 16 causing air to flow through vacuum tube 26 and check valve 27 from cavity 42 to vacuum pump 22, which air is then expelled into the interior of post 14. The resulting vacuum in cavity 42 draws the patient's residual limb 40 into socket 12 and into tight coupling to permit use of the prosthetic device 10 for ambulatory activity. As seen in FIG. 4B, the residual limb 40, when drawn into this vacuum induced contact with socket 12, is tightly coupled to socket 12.

Referring now to FIG. 5, an alternative embodiment of invention may be described. In this alternative embodiment post 14 is simplified by not including therein vacuum pump 22 or battery 20. Rather, post 14 contains only vacuum line 26 coupled to the interior of socket 12. Vacuum line 26 connects to a vacuum orifice coupler 50/52, which includes two parts. A first part of coupler 50/52 is a check valve 50 permitting airflow from chamber 12 through vacuum line 26 but blocking airflow from the exterior environment into vacuum line 26 and socket 12. Coupler 50/52 also includes an orifice 52 for receiving a vacuum line from an external portable vacuum pump 56. Vacuum pump 56 includes a vacuum line 54 with a coupler 55 on the end thereof for connection to coupler 52. The interior of vacuum pump 56 includes a battery 60, a vacuum pump 62, and a control switch 66. Battery 60 is connected electrically to vacuum pump 62 via electrical connections identical to those described above with reference to FIGS. 2 to 4B, and vacuum line 54 is connected to the inlet port of vacuum pump 62.

Portable vacuum pump can thus be used to draw vacuum from socket 12 by connecting coupler 55 to coupler 52, then actuating switch 66 to activate vacuum pump 62 and draw vacuum through vacuum line 54. An advantage of a portable vacuum pump as shown in FIG. 5 is that the weight of the battery 60 and vacuum pump 62 do not remain in post 14, and thus are not a burden for the patient during the patient's normal ambulatory activities. Although the weight of these components may be relatively small, removing these components from post 14 does remove weight. Also, a patient with a relatively long residual limb and thus short post 14 may not have sufficient volume in the post to enclose the motor and/or battery therein as shown in the preceding drawings. In such a case the portable unit may be utilized to provide a portable vacuum source for the patient. Additionally, another important application for the portable pump relates to above the knee amputees. In such an application, there is not typically enough room to incorporate a vacuum system between a prosthetic knee coupler and the end of the user's socket (12). It will be noted that there will almost always be enough room between the knee coupler and the prosthetic foot to install a vacuum system; however, the wires and tubes have to be protected against the constant flexing and extending of the knee unit, and thus it may be preferred to use a portable pump as illustrated in FIG. 5 for such applications, making elevated vacuum technology potentially more reliably available to above knee amputees.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art.

For example, while the invention has mainly been illustrated for the case of a below-the-knee leg amputee, above-the-knee amputees may also benefit from the invention. Furthermore, upper limb amputees are also important possible beneficiaries of the invention.

A further potential enhancement of the elevated vacuum system, involves the inclusion of a second port to the prosthetic socket and a second hole in the socket itself. The second port has a flexible tube connected to a quick-disconnect coupler including a one-way valve, much as is used in air system at service stations. The second port can provide three important improvements. 1) It will allow a patient to attach a vacuum gauge (temporarily) to see what level of vacuum has been achieved with the electric pump. 2) Once pumped down, the patient can also see if the vacuum is holding, as leaks would be apparent from changes in pressure. 3) The second port would permit a back-up vacuum source to be attached to the prosthetic socket in case of internal pump failure or duckbill valve leak. In the latter circumstance the patient could put tape over the primary hole in the socket, thus closing it off, and then use a hand held electric pump, or alternately use a hand operated pump, to draw vacuum from the socket until the primary system can be serviced.

In addition, technology for the care of wounds has now expanded to include the use of vacuum pressure to improve healing of open tissue ulcerations. While this technology is still evolving, early results indicate that it is an important adjunct in wound care. The vacuum pump of the present invention may therefore be utilized not only for persons who wear artificial limbs but also persons who have wounds and wish to utilize vacuum in treatment of those wounds. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A prosthetic limb, comprising
a socket adapted to receive at least a portion of a patient's residual limb,
a vacuum port in said socket for evacuation of air therefrom,
a post having an internal cavity, said post having a length and extending from a distal end of said prosthetic socket to an opposite end to be coupled to a prosthetic component,
an electrically powered vacuum pump located within said internal cavity of said post, said vacuum pump having an air intake coupled to said vacuum port of said socket, and
an electrical power source connectable to said vacuum pump for powering said vacuum pump to evacuate said socket while a patient's residual limb is engaged therein.

2. The prosthetic limb of claim 1 further comprising an electrical switch electrically interposed between said electrical power source and said vacuum pump.

3. The prosthetic limb of claim 1 wherein said electrical power source is located within said internal cavity of said post.

4. The prosthetic limb of claim 1 wherein said electrical power source is located externally to said post.

5. The prosthetic limb of claim 2 wherein said electrical switch is incorporated into said post so as to be accessible from the exterior of said prosthetic limb.

6. The prosthetic limb of claim 1 wherein said electrical power source is a battery compatible with the 9 volt standard size.

7. The prosthetic limb of claim 1 wherein said electrical power source is a rechargeable battery.

8. The prosthetic limb of claim 7 wherein said battery is compatible with the 9 volt standard size.

9. A prosthetic limb, comprising
a socket adapted to receive at least a portion of a patient's residual limb,
a vacuum port in said socket for evacuation of air therefrom,
a post having an internal cavity, said post having a length and extending from a distal end of said prosthetic socket to an opposite end to be coupled to a prosthetic component,
an electrically powered vacuum pump located within said internal cavity of said post, said vacuum pump having an air intake coupled to said vacuum port of said socket by a vacuum line,
an electrical power source located within said internal cavity of said post and connectable to said vacuum pump, and
an electrical switch electrically interposed between said electrical power source and said vacuum pump for actuating said vacuum pump to evacuate said socket while a patient's residual limb is at least partially inserted therein.

10. The prosthetic limb of claim 9 wherein said electrical switch is incorporated into said post so as to be accessible from the exterior of said prosthetic limb.

11. The prosthetic limb of claim 9 wherein said electrical power source is a battery compatible with the 9 volt standard size.

12. The prosthetic limb of claim 11 wherein said battery is rechargeable.

13. The prosthetic limb of claim 9 further comprising a check valve installed in said vacuum line to prevent airflow into said socket.

14. A prosthetic limb, comprising a socket adapted to receive at least a portion of a patient's residual limb, a post having an internal cavity, said post having a length and extending from a distal end of said prosthetic socket to an opposite end to be coupled to a prosthetic component, a vacuum port in said socket for evacuation of air therefrom, said vacuum port extending from an interior of said socket into said internal cavity of said post, an electrically powered vacuum pump located within said internal cavity of said post, said vacuum pump coupled to said vacuum port of said socket by a vacuum line that that travels through said internal cavity of said post, and an electrical power source for powering said vacuum pump to withdraw air from said socket.

15. The prosthetic limb of claim 14 wherein said electrical power source is located within said internal cavity of said post.

16. The prosthetic limb of claim 14 wherein said electrical power source is located externally to said post.

17. The prosthetic limb of claim 14 wherein said electrical power source is a battery.

* * * * *

(12) EX PARTE REEXAMINATION CERTIFICATE (9322nd)
United States Patent
Haines

(10) Number: US 7,914,586 C1
(45) Certificate Issued: Oct. 2, 2012

(54) PROSTHETIC DEVICE UTILIZING ELECTRIC VACUUM PUMP

(75) Inventor: Wilbur A. Haines, Indianapolis, IN (US)

(73) Assignee: The Ohio Willow Wood Company, Mount Sterling, OH (US)

Reexamination Request:
No. 90/009,949, Sep. 8, 2011

Reexamination Certificate for:
Patent No.: 7,914,586
Issued: Mar. 29, 2011
Appl. No.: 11/149,858
Filed: Jun. 10, 2005

(51) Int. Cl.
*A61F 2/48* (2006.01)
*A61F 2/60* (2006.01)
*A61F 2/78* (2006.01)

(52) U.S. Cl. .......................................... 623/24; 623/33

(58) Field of Classification Search .................. None
See application file for complete search history.

(56) References Cited

To view the complete listing of prior art documents cited during the proceeding for Reexamination Control Number 90/009,949, please refer to the USPTO's public Patent Application Information Retrieval (PAIR) system under the Display References tab.

*Primary Examiner* — David O. Reip

(57) ABSTRACT

An artificial limb using a vacuum attachment principle is provided with an electrically activated pump that may be readily incorporated into the artificial limb or into a separate portable device. Because the electrically activated pump does not require manual manipulation to create vacuum, it is substantially easier to use than a manual pump. Due to the small size and small battery required by the electrically activated pump disclosed here, it may be readily incorporated into a prosthesis.

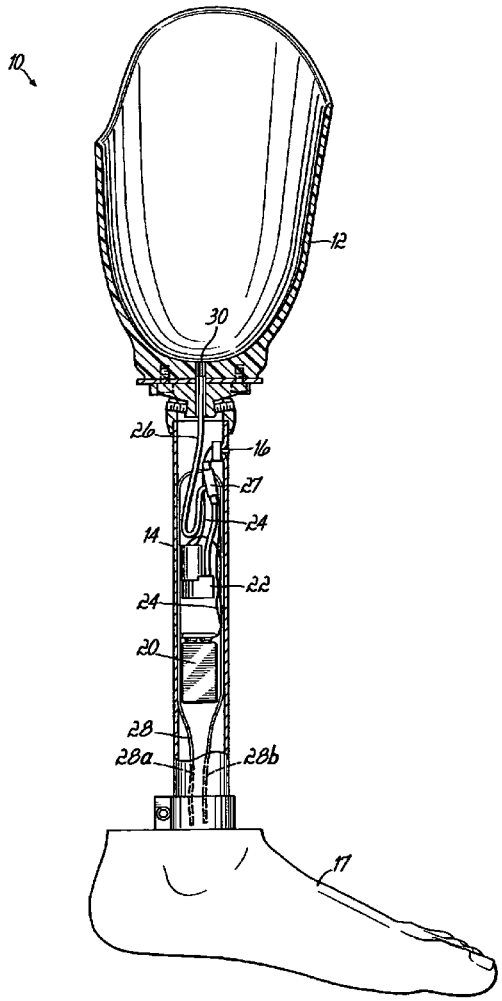

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 9 and 14 are determined to be patentable as amended.

Claims 2-8, 10-13 and 15-17, dependent on an amended claim, are determined to be patentable.

New claims 18-20 are added and determined to be patentable.

1. A prosthetic limb, comprising
a socket adapted to receive at least a portion of a patient's residual limb,
[a vacuum port in said socket for evacuation of air therefrom,]
a post having an internal cavity, said post having a length and extending from a distal end of said prosthetic socket to an opposite end to be coupled to a prosthetic component,
*a vacuum port in said socket for evacuation of air therefrom, said vacuum port extending from an interior of said socket into said internal cavity of said post,*
an electrically powered vacuum pump located within said internal cavity of said post, said vacuum pump having an air intake [coupled to] *in fluid communication with* said vacuum port of said socket, and
an electrical power source connectable to said vacuum pump for powering said vacuum pump to evacuate said socket while a patient's residual limb is engaged therein.

9. A prosthetic limb, comprising
a socket adapted to receive at least a portion of a patient's residual limb,
[a vacuum port in said socket for evacuation of air therefrom,]
*a coupling device attached to a distal end of said socket and adapted to couple said socket to a post element of said residual limb,*
a post having an internal cavity, said post having a length and extending from [a distal end of] said [prosthetic socket] *coupling device* to an opposite end to be coupled to a prosthetic component,
*a vacuum port in said socket and a vacuum port in said coupling device, said vacuum ports cooperating to form a vacuum passageway between an interior of said socket and said internal cavity of said post,*
an electrically powered vacuum pump located within said internal cavity of said post, said vacuum pump having an air intake [coupled to said vacuum port of said socket by a vacuum line],
*a vacuum line located within said internal cavity of said post and providing a path of fluid communication between said vacuum pump air intake and said interior of said socket via said vacuum passageway,*
an electrical power source located within said internal cavity of said post and connectable to said vacuum pump, and
an electrical switch electrically interposed between said electrical power source and said vacuum pump for actuating said vacuum pump to evacuate said socket while a patient's residual limb is at least partially inserted therein.

14. A prosthetic limb, comprising
a socket adapted to receive at least a portion of a patient's residual limb,
*a male coupling element attached to a distal end of said socket,*
a post having an internal cavity, said post having a length and extending from [a] *said* distal end of said prosthetic socket to an opposite end to be coupled to a prosthetic component,
*a female coupling element attached to a proximal end of said post and cooperating with said male coupling element to couple said post to said socket,*
[a] vacuum [port] *ports in each of* said socket [for evacuation of air therefrom,] *and said male and female coupling elements,* said vacuum [port extending from] *ports aligned after said prosthetic limb is assembled and cooperating to form a vacuum passageway between* an interior of said socket [into] *and* said internal cavity of said post,
an electrically powered vacuum pump located within said internal cavity of said post, [said vacuum pump coupled to said vacuum port of said socket by a vacuum line that that travels through said internal cavity of said post], [and]
*a vacuum line located within said internal cavity of said post and providing a path of fluid communication between said vacuum pump and said interior of said socket via said vacuum passageway, and*
an electrical power source for powering said vacuum pump to withdraw air from said socket.

18. *The prosthetic limb of claim 1 wherein a vacuum line is located within said internal cavity of said post and connects said vacuum pump to an orifice located in said vacuum port in said prosthetic socket.*

19. *The prosthetic limb of claim 9 wherein one end of said vacuum line passes through said vacuum passageway and connects said vacuum pump to an orifice located in said vacuum port in said prosthetic socket.*

20. *The prosthetic limb of claim 14 wherein one end of said vacuum line passes through said vacuum passageway and connects said vacuum pump to an orifice located in said vacuum port in said prosthetic socket.*

\* \* \* \* \*